(12) United States Patent
Swartzlander, Jr.

(10) Patent No.: US 10,393,643 B2
(45) Date of Patent: Aug. 27, 2019

(54) OPTICAL VORTEX CORONAGRAPH SCATTEROMETER

(71) Applicant: Grover A. Swartzlander, Jr., Rochester, NY (US)

(72) Inventor: Grover A. Swartzlander, Jr., Rochester, NY (US)

(73) Assignee: Rochester Institute of Technology, Rochester, NY (US)

( * ) Notice: Subject to any disclaimer, the term of this patent is extended or adjusted under 35 U.S.C. 154(b) by 0 days.

(21) Appl. No.: 15/698,238

(22) Filed: Sep. 7, 2017

(65) Prior Publication Data

US 2018/0067036 A1     Mar. 8, 2018

Related U.S. Application Data

(60) Provisional application No. 62/384,457, filed on Sep. 7, 2016.

(51) Int. Cl.
    *G01N 15/14*     (2006.01)

(52) U.S. Cl.
    CPC .................... *G01N 15/1434* (2013.01)

(58) Field of Classification Search
    CPC .... G01N 15/1434; G01B 11/00; H01L 22/00; G02B 5/00
    USPC ................... 356/338–339, 342, 344
    See application file for complete search history.

(56) References Cited

U.S. PATENT DOCUMENTS

| | | | |
|---|---|---|---|
| 3,624,835 A | 11/1971 | Wyatt | |
| 4,710,642 A | 12/1987 | McNeil | |
| 5,241,369 A | 8/1993 | McNeil et al. | |
| 5,659,420 A * | 8/1997 | Wakai ................. | G01B 11/026 356/511 |
| 6,597,446 B2 | 7/2003 | Klooster et al. | |
| 8,139,232 B2 | 3/2012 | Wolf et al. | |
| 9,310,286 B2 | 4/2016 | Jacobs et al. | |
| 10,101,671 B2 | 10/2018 | Quintanilha et al. | |

(Continued)

FOREIGN PATENT DOCUMENTS

| | | |
|---|---|---|
| CN | 103983546 | 8/2014 |
| EP | 2975378 | 1/2016 |

OTHER PUBLICATIONS

Heterodyne near-field scattering, Appl. Phys. Lett. 81, 4109 (2002).

(Continued)

*Primary Examiner* — Isiaka O Akanbi

(74) *Attorney, Agent, or Firm* — Bond, Schoeneck & King, PLLC; Joseph Noto

(57) ABSTRACT

An optical vortex coronagraph scatterometer including a light source of wavelength $\lambda$, a scattering cell in optical communication with the light source, a circular aperture having a radius R at a distance d from the scattering cell in optical communication with the light source, a pivot point between the circular aperture and the scattering cell allowing relative movement of the light source and the scattering cell with respect to the circular aperture, a first lens at a focal length $f_1$ between the circular aperture and an optical vortex element, and a second lens at a focal length $f_2$ between the optical vortex element and a detector; and method for determining a scattering spectra at low and zero angles is disclosed.

8 Claims, 3 Drawing Sheets

(56) References Cited

U.S. PATENT DOCUMENTS

| | | | |
|---|---|---|---|
| 2007/0013999 A1* | 1/2007 | Marks | B82Y 20/00 |
| | | | 359/368 |
| 2009/0279090 A1 | 11/2009 | Wolf et al. | |
| 2010/0045980 A1* | 2/2010 | Tsukuda | G01N 21/251 |
| | | | 356/319 |
| 2013/0304424 A1 | 11/2013 | Bakeman et al. | |
| 2017/0184981 A1 | 6/2017 | Quintanilha et al. | |
| 2017/0348872 A1 | 12/2017 | Suzuki et al. | |

OTHER PUBLICATIONS

A schlieren method for ultra-low—angle light scattering measurements, Europhys. Lett. 63 , 220 (2003).

* cited by examiner

OPTICAL VORTEX CORONAGRAPH SCATTEROMETER

CROSS REFERENCE

This application claims the benefit of the filing date of U.S. Provisional Patent Application Ser. No. 62/384,457, filed Sep. 7, 2016, which is hereby incorporated by reference in its entirety.

This invention was made with government support under grant number Grant No. ECCS-1309517 awarded by the National Science Foundation. The government has certain rights in this invention.

FIELD

The present disclosure relates to an optical vortex coronagraph scatterometer and method, and in particular to an optical vortex coronagraph scatterometer and method capable of accurately measuring the complete scattering spectrum at the zero, low and high angles.

BACKGROUND

Scatterometers are used in many industrial applications from pharmaceuticals, paint, food production, and surface inspection owing to the ability to quickly and reliably characterize the size and distribution of microscopic particles. Scatterometers obviate the need for direct imaging to characterize optical or geometric properties of single or multiple scatterers. Typical devices measure the intensity of light as a function of position (e.g., angle) at a given distance from the scattering sample. This measurement, called the scattering spectrum, is typically made by use of a collimated or quasi-collimated laser beam or other quasi-monochromatic light source. Typical devices are unable to accurately determine scattering spectra at very low angles where the unscattered light is much brighter than the scattered light.

Intensity measurements of scattered laser light at various angles (the angular spectrum) may be used to measure surface contamination, characterize the clarity of transparent solids, evaluate the bidirectional reflectance distribution function (BRDF), or determine the sizes of particles suspended in a liquid or solid. Size determination may be made for particles of a known refractive index by fitting the measured angular spectrum data to models based on Mie scattering theory, and thus, it is important to record a full distribution of angles. However, in the weak scattering regime typical of this method, it is difficult to distinguish low-angle scattered light from the more intense unscattered laser light, especially near the zero angle. That is, the signal is lost in the glare of the illumination source. This resulted in inaccurate low-angle scattering values or estimates which are used to approximate the needed data.

The art lacks the ability to accurately measure the full scattering spectrum, particularly at very low or zero scattering angles.

SUMMARY

In accordance with one aspect of the present disclosure, there is provided an optical vortex coronagraph scatterometer including a light source of wavelength $\lambda$; a scattering cell in optical communication with the light source; a circular aperture having a radius R at a distance d from the scattering cell in optical communication with the light source; a pivot point between the circular aperture and the scattering cell allowing relative movement of the light source and the scattering cell with respect to the circular aperture; a first lens at a focal length $f_1$ between the circular aperture and an optical vortex element; and a second lens at a focal length $f_2$ between the optical vortex element and a detector.

In accordance with another aspect of the present disclosure, there is provided a method for measuring the angular spectrum of scattered light, including providing an optical vortex coronagraph scatterometer including: a light source; a scattering cell in optical communication with the light source; a circular aperture having a radius R at a distance d from the scattering cell in optical communication with the light source; a pivot point between the circular aperture and the scattering cell allowing relative movement of the light source and the scattering cell with respect to the circular aperture; a first lens at a focal length $f_1$ between the circular aperture and an optical vortex element; a second lens at a focal length $f_2$ between the optical vortex element and a detector; transmitting light from the light source through the scattering cell at a first angle of the pivot point; transmitting light from the light source through the scattering cell at a second angle of the pivot point; and measuring the low-angle scattered light from the scattering cell.

These and other aspects of the present disclosure will become apparent upon a review of the following detailed description and the claims appended thereto.

DETAILED DESCRIPTION

Figure 1:
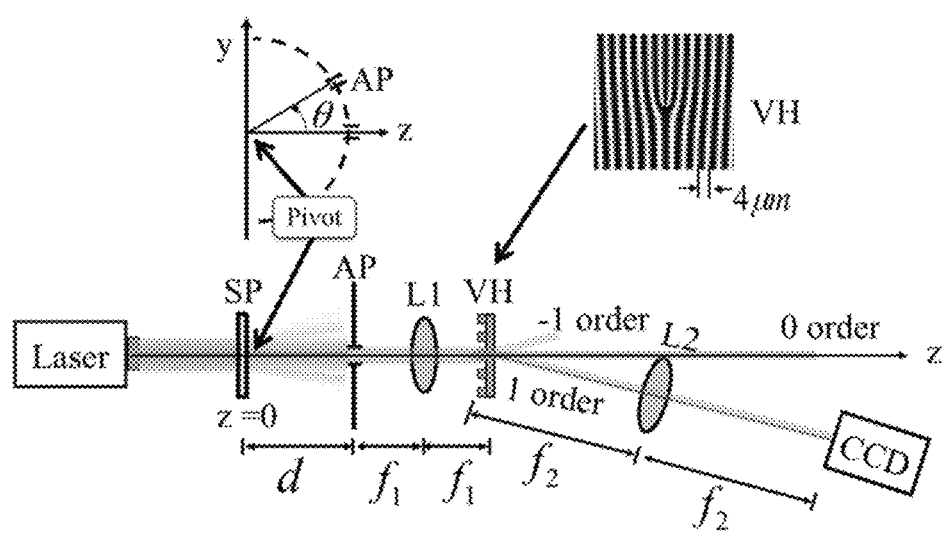
FIG. 1 is a schematic of an optical vortex coronagraph scatterometer in accordance with an embodiment of the present invention.

The present invention relates to an optical vortex coronagraph scatterometer including a light source, such as a collimated laser, of wavelength $\lambda$; a scattering cell in optical communication with the light source; a pivot point between the light source and the scattering cell allowing relative movement of the light source and the scattering cell; a circular aperture having a radius R at a distance d from the scattering cell in optical communication with the light source; a first lens at a focal length $f_1$ between the circular aperture and an optical vortex element; a second lens at a focal length $f_2$ between the optical vortex element and a detector that measures the scattered light. The lenses are preferably relatively free from aberrations at the source wavelength, computer-optimized achromatic doublet lenses or better are preferred. Greater precision of the angular spectrum is achieved by use of such high quality optics, as well as antireflection coatings on all optical surfaces (e.g., lenses, sample cell, vortex element). These steps better allow the system to approach the theoretical performance, which provides exceptionally high contrast between the unscattered light and scattered light in the interior of the ring of fire. Theory suggests that no unscattered light will appear in this region, resulting in the ratio of scattered to unscattered power equal to infinity, assuming a perfect optical system. In practice a ratio of 10 to 1000 may be sufficient, depending on the size and distribution of scatterers. A contrast of 200 was measured for the Example shown in FIG. 3. That is, the vortex scatterometer suppressed the unscattered low angle laser light by a factor of 200. The detector may be a single element such as a photodiode or an array of elements such as a CCD or CMOS sensor array. The detector is placed in the back focal plane of a 4-f imaging system composed of lenses of focal length $f_1$ and $f_2$. The aperture (AP in FIG. 1) of radius R is placed in the front focal plane of the 4-f system. The value of R is less than the radial size of the collimated laser beam, w, and larger or on the order of the transverse coherence size, $\lambda d/2w$. The vortex element is placed at the common focal point between the two lenses of the 4-f system. The vortex element is designed to change the phase of the electric field at the input face with a complex transmission function given by $t(x,y)=\exp(i\,m\,\theta)$, where m is an even nonzero integer (for example, m=−4, −2, 2, or 4), $\theta=\arctan(y/x)$, and i is the imaginary number (square root of −1). The vortex element designed for use at the wavelength $\lambda$ may be composed of a holographic element (as depicted in the Example in FIG. 1), spiral phase plate, polarization diffraction grating (also called various names such as q-plate), a subwavelength diffraction grating, and other methods that achieve the above transmission function. The axis of the vortex element is aligned with the center of the beam transmitted through the aperture (AP) to create the so-called "ring of fire" depicted in FIGS. 2 and 3. The integrated power internal to this ring is directly proportional to the scattering power, thereby allowing discrimination between scattered and unscattered light. The inner radius of the ring of fire is equivalent to the magnified radius of the aperture AP: $R'=(f_2/f_1)R$. The radius of the detection region is made smaller than R', with the detection made in the central region of the dark zone. For the example shown in FIG. 3, the integration detection area was roughly equal to $A=(\frac{1}{2})\pi R'^2$. At large scattering angles the ring of fire may seem to disappear because the fraction of available unscattered light becomes vanishingly small. At such large scattering angles the positioning of the vortex element is not critical. An approximate angle distinguishing this boundary is 1.5 to 3 times the divergence angle of the unscattered light source. For example, in FIG. 3 the beam divergence angle is 5 milliradians and the ring of fire disappears at approximately 8 milliradians. The normalized value of the scattering spectrum at a given angle is calculated from four measurements: $I(\theta)$, $J(\theta)$, I', and J', where $I(\theta)$ is the integrated power across the detection area A (for example, $A=(\frac{1}{2})\pi R'^2$) centered within the ring of fire for an arbitrary scattering angle, $J(\theta)$ is a measure of noise across an equivalent area A, I' is the integrated power across the entire beam in the detector plane across a large area A'>>A (e.g., an area equal to A'=32A was used in FIG. 3), and J' is a measure of noise across an equivalent area A'. The normalized scatter signal at a given angle $\theta$ is determined from the ratio $\eta(\theta)/\eta(\theta\approx 0)$, where $\eta(\theta)=(I(\theta)-J(\theta))/(I'-J')$. A representative normalized scattering spectrum is depicted in FIG. 3. The values of $\eta(\theta\approx 0)$ is made at or near a zero scattering angle. For example, in FIG. 3 the value of $\eta(\theta\approx 0)$ was made at $\theta=1.1$ milliradians to avoid anomalous values that may occur at $\theta=0$ owing to Anderson localization or other phenomena not explained by Mie theory. The purpose of the normalization constant, $\eta(\theta\approx 0)$, is to provide a value of unity ($\eta(\theta)/\eta(\theta\approx 0)=1$) at or near the zero scattering angle, in agreement with the normalized Mie scattering spectrum.

The present invention relates to method for measuring the angular spectrum of scattered light, including providing an optical vortex coronagraph scatterometer, such as that disclosed herein; transmitting light from the light source through the scattering cell at a first angle of the pivot point; transmitting light from the light source through the scattering cell at a second angle of the pivot point; and measuring the low-angle scattered light from the scattering cell. The values of $I(\theta)$ are $J(\theta)$ are determined from measurements made by changing the relative angle $\theta$ between arm-1 composed of the light source and scattering cell, and arm-2 composed of the pivot point, aperture, lens-1 and lens-2, vortex element, and detector. To correct small misalignments during this operation, the vortex element may be placed on a two or three dimensional translation stage to return the vortex axis to the optimal position that provides the minimum value of $I(\theta)$. The stage should be capable of translational increments amounting to a small percentage (e.g., less than 5%) of the value $\lambda f_1/R$.

In an embodiment, an optical vortex coronagraph is placed on a goniometer arm (arm-2) with a scattering cell at a pivot point allowing relative movement of the light source and sample. The sample containing scatterers is illuminated with a collimated or quasi-collimated laser beam and the light transmitted through the system is recorded on a photodetector or camera. The system is unique because it allows a measurement of the full scattering spectrum, including the previously unobtainable zero and near-zero low-angle scattering spectra.

The scattered and unscattered laser light from the sample is separated by the present invention by use of an optical vortex element, such as an optical vortex mask, vortex hologram, spiral phase plate, vortex subwavelength diffraction grating, or q-plate, which relies on the different spatial coherence properties of the scattered and unscattered laser light to separate the two. This difference allows forward scattered light measurements at the zero angle and low angles, which agree with predicted values for known particle sizes across a range of concentrations. A scatterometer in accordance with an embodiment of the present invention uses an optical vortex coronagraph (OVC) mounted on a goniometer arm to obtain the scattering spectrum. The original manifestation of an OVC is designed to distinguish two unresolvable and mutually incoherent sources. In this application the OVC functions as a spatial coherence filtering instrument. The OVC has the ability to distinguish a point source (equivalently, a collimated spatially coherent laser beam) from a spatially incoherent extended source such as scatterers. As part of a scatterometer, the optical vortex coronagraph distinguishes the highly coherent illumination source (e.g., a laser) from the scattering volume which appears to the instrument as a low coherence extended light source.

In an embodiment, the scatterometer has an optical vortex coronagraph placed on a goniometer arm (arm-2) to measure the scattering spectrum at both low and high angles. The low-angle suppression of unscattered light allows excellent agreement between Mie theory and fitted experimental results. This type of device may be particularly useful in industrial applications where the scattering spectrum is routinely used to characterize particle sizes or where small scattering superimposed on either a specular reflection or a transmitted beam must be measured.

An embodiment of an optical vortex coronagraph may be described as a 4-f Fourier optics system composed of two lenses of focal lengths $f_1$ and $f_2$, and a vortex mask at the focal plane (FP), as shown, for example in FIG. 1. The entrance pupil (PP1) and exit pupil (PP2) are located at the outer focal points. The vortex mask has a transmission function $t(x,y)=\exp(im\phi)$, where m is a nonzero even integer called the vortex charge, and $\phi$ is the azimuth angle about the optical axis. The intensity distributions and false-color phase profile for the case m=2 are depicted in FIG. 1(a-c) when a uniform coherent plane wave illuminates a circular aperture of radius R placed at PP1. A remarkable diffraction pattern occurs at PP2 (FIG. 1c) when the beam produces a diffraction-limited spot at the center of the vortex mask. Rather than forming a uniformly illuminated disk (as occurs if the mask is removed), it forms a dark circular "ring of fire" with a black central disk of radius $R'=Rf_2/f_1$. In contrast, when the illumination originates from a spatially incoherent extended source (e.g., scattering particles), the disk will have a nonzero intensity. In the scattering experiment described below, light incident upon the entrance pupil may be described by a superposition of incoherent scattered light and coherent unscattered light. Ideally the two sources spatially separate at the exit pupil with coherent light forming the ring of fire and incoherent light forming a bright disk, thereby allowing a separate measurement of only the incoherent light. In practice, some coherent light may "leak" into the central disk owing for example to wavefront errors or optical misalignments. For a circular aperture of radius R in PP1 illuminated by a monochromatic plane wave directed parallel to the optical axis, the optical field in the focal plane, FP, at the output face of the mask may be written:

$$E(\rho,\phi)=2\pi R k_\rho^{-1} J_1(k_\rho R)\exp(im\phi) \quad (1)$$

where we assume paraxial rays and write $k_\rho=(2\pi/\lambda)(\rho/f_1)$, where $J_1$ is the first order Bessel function of the first kind, $(\rho,\phi)$ are the polar coordinates in the focal plane, and $\lambda$ is the wavelength of light. The optical field at the output pupil (PP2) is represented by the Fourier transform of equation (1):

$$E(r, \phi') = \begin{cases} 0 & r < R' \\ \frac{R'}{r} Z^1_{|m|-1}\left(\frac{R'}{r}\right) e^{im\phi'} & r > R' \end{cases} \quad (2)$$

where $Z_a^b$ are the radial Zernike polynomials, $|m|=2, 4, 6, \ldots$, and $(r,\phi')$ are the polar coordinates in the plane PP2. A black disk in the region $r<R'$ is surrounded by a ring of fire at $r>R'$. For example, if m=2, the ring of fire is described by $E(r>R',\phi')=(R'/r)^2 \exp(i2\phi')$. In contrast, for an incoherently illuminated aperture, the irradiance distribution in the exit pupil may be approximately described by the geometric image of the entrance pupil.

FIG. 1 shows an embodiment of an optical vortex coronagraph scatterometer with a sample cell (SP) at the pivot point, 0, illuminated by a collimated laser. The remaining components swing on a goniometer arm by an angle. Aperture (AP), lens L1 and L2 of focal lengths $f_1$ and $f_2$, vortex generator (10 mm×10 mm, 4 µm grating period vortex hologram (VH) with charge m=2), and CCD camera in the exit pupil plane with attenuator.

Figure 2:
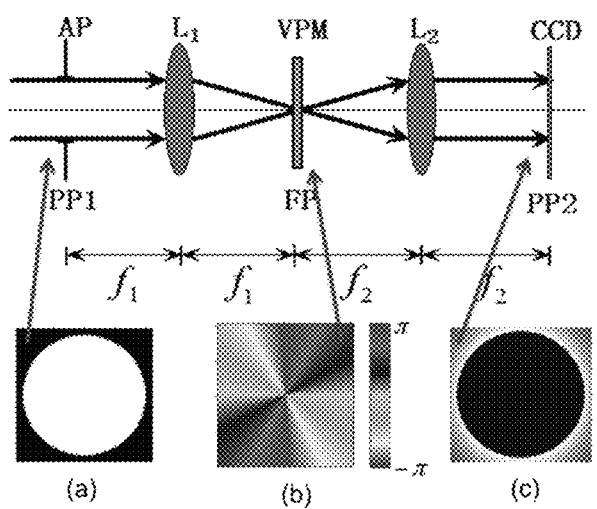
FIG. 2 is a schematic of an optical vortex coronagraph in accordance with an embodiment of the present invention.
Figure 3:
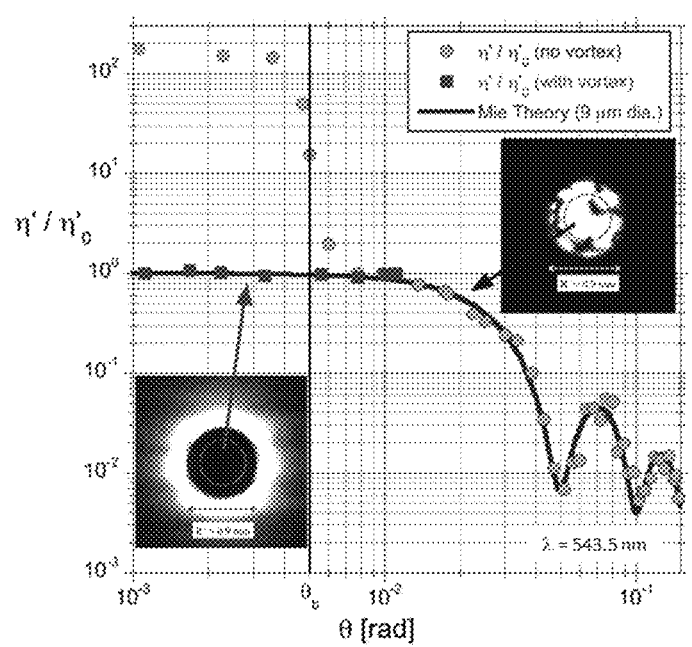
FIG. 3 is a scattering spectrum of experimental results from Example 1.

FIG. 2 top is a schematic of an embodiment of an optical vortex coronagraph with entrance pupil PP1, exit pupil PP2, and vortex phase mask (VPM) in the focal plane (FP). Achromatic lenses $L_1$ and $L_2$ with focal lengths $f_1$ and $f_2$. Insert (a) shows a front view of the circular aperture (AP) at PP1 of radius R. Insert (b) shows a front view of a false color phase profile of VPM. Insert (c) shows a dark disk of radius $R'=Rf_2/f_1$ in the exit pupil owing to VPM and an on-axis coherent light source.

FIG. 3 shows an experimental scattering spectrum for 9 µm polystyrene spheres in water in accordance with the Example. Measured values with the vortex aligned with the beam axis are shown as red squares and measured values without the vortex aligned with the beam axis are shown as gray circles. Mie theory predicted values are shown by the solid lines. Error bars (not shown) are smaller than the data points. Inset images represent typical recorded frames.

This device may be used as a standard scatterometer for a vast number of industrial applications to measure very low angle scattered light. All other devices stop working at the low angle limit.

The system for example may replace a typical industrial scatterometer for measuring a dilute suspension of particles in a liquid, surface or bulk scattering defects, either in transmission or reflection. Through low-angle scattering the present invention can detect particle sizes typically in the 30 µm to 3 mm range.

The disclosure will be further illustrated with reference to the following specific example. It is understood that these examples are given by way of illustration and are not meant to limit the disclosure or the claims to follow.

Example 1

This Example describes experimental results whereby a vortex coronagraph is used to measure the angular spectrum of scattered light, including at the zero angle. To measure the angular spectrum of scattered light an optical vortex coronagraph, as illustrated in FIG. 1 was used. A green HeNe laser ($\lambda$=543.5 nm) having a collimated beam radius (w=0.88 mm) was made normally incident to a thin scattering cell of inner path length $L_c$=0.50 mm. The cell contained a dilute water suspension of polystyrene spheres (certified mean diameter $D_s$=8.93 µm±0.07 µm, refractive index $n\approx1.597$) at an approximate concentration of $C=5\times10^3$ mm$^{-3}$=0.16$C_0$ where $C_0=4/\pi D_s^2 L=3.1\times10^4$ mm$^{-3}$ is the scattering extinction parameter. A portion of the scattered light is transmitted through an aperture (AP) with diameter $D_{AP}$=0.30 mm at a distance d=213 mm from the sample. According to the van Cittert-Zernike theorem, the coherence diameter of the extended scattering source, as measured at AP was $D_{coh}\approx\lambda d/w$=0.13 mm. The scattered light transmitted through AP has a moderately low coherence because $D_{AP}/D_{coh}$=2.3. A lens L1 ($f_1$=100 mm, $f_1^\#$=3.9) focuses the light onto the axis of an m=2 vortex hologram (VH) having a binary amplitude period of $\Lambda$=4 µm (see inset of FIG. 1), creating a partially coherent first order diffracted beam that is characterized by an optical vortex with m=2. The diameter of the Airy disk, $2.44\lambda f_1/D_{AP}$=663 µm, covers 166 grating lines, and therefore the beam is well-sampled by the hologram. By displacing the beam focus from the vortex axis, the hologram can be made to function as a simple diffraction grating. Another lens L2 ($f_2$=300 mm, $f_2^\#$=5.9) collects the light diffracted into the first order ($\psi$=7.8°), rendering a ring of fire on a focal plane detector (CCD). Achromatic lenses were used to lessen spherical aberrations. An attenuator at the detector is used to provide unsaturated images with exposure times of roughly one second. Owing to the magnification factor $f_2/f_1$, the dark disk is expected to have a diameter of 3$D_{AP}$ at the detector. A mounting arm holding all the elements behind the sample cell (AP, L1, etc.) freely pivots by a horizontal angle θ about the exit face of the cell (see FIG. 1). The unscattered beam at AP has an angular half-width of $\theta_b\approx$5 mrad.

Low-angle measurements ($|\theta|\leq 2\theta_b$) were made while insuring the beam focus was centered on the holographic vortex center. This condition occurs when the power is a minimum within the dark disk described above. Under perfect operating conditions the power within that zone may be entirely attributed to scattering, and the integrated recorded intensity across that region will be a measure of the scattered light at a given value of θ. For $|\theta|>\theta_b$ the ring of fire disappears for lack of unscattered coherent light, and an image of a speckled or a quasi-uniformly illuminated aperture AP appears at the detector. Typical recorded images for $|\theta|<\theta_b$ and $|\theta|>\theta_b$ are shown as insets into FIG. 3.

An SBIG MODEL ST 402XME CCD detector, cooled to 7.5° C. was used, and subtracted dark frame images from the recorded frames. The detector area has 765×510 pixels with a pitch of 9 μm. Image processing was used to compute the relative integrated beam power across a given region. The average noise power was obtained by summing the pixel values over a region far from the ring of fire. Dividing by the integration area provides the average noise intensity, $I_{noise}$ for a given frame. A value representing the total integrated beam power was obtained by first summing the pixel values across a circle centered on the ring of fire and having a radius corresponding the 4R', and then subtracting the estimated noise power. This captures at least 97% of the power without integrating over excessive stray light and detector noise. Likewise, the beam power within the ring of fire was obtained by summing over the signal and subtracting the estimated noise power. To partially circumvent confounding effects such as aberrations and misalignments, we integrated over the central half area of the ring of fire with radius: $R_{int}=R'/\sqrt{2}$. (corrected a typo here and below) The calculated fraction of intensity scattered into the central region of the ring of fire may be expressed according to $$\eta = I_{in}/I_0 = \int_0^{R_{int}} (I(r) - I_{noise}) r dr \bigg/ \int_0^{4R'} (I(r) - I_{noise}) r dr \quad (3)$$

The zero angle value of the scattering spectrum (θ=0) was measured as $\eta_0$=0.15%. This value is in close agreement with the theoretical value of 0%. To compare values of η measured with different exposure times, T, and optical density of the attenuator, α, the following scaling was used:

$$\eta'=10^{\alpha}\eta T_0/T \quad (4)$$

where $T_0$=1 sec is a typical exposure time. An average value of η' was calculated from ten recordings at each angle, resulting in error bars smaller than the data points depicted in FIG. 3. Finally, the experimental values were fit to Mie scattering theory, adjusting for the minimum variance. The ratio $\eta'/\eta'_0$ is plotted in FIG. 3, where $\eta'_0$=2.8 is the value of η' near θ=0. The square (red) low-angle data points were measured by carefully aligning the vortex mask with the center of the scattered beam as described above, whereas the circular (gray) data points were measured with the vortex axis displaced from the beam (the vortex alignment has a negligible effect for $|\theta|>2\theta_b$). In the latter case the vortex hologram acts as a linear grating, allowing a comparison between the vortex-filtered and unfiltered scattering data at small angles. The plots in FIG. 3 provide clear evidence of vortex suppression of more than two orders of magnitude across the entire low-angle range. For comparison, FIG. 3 also includes a plot of the predicted scattering spectrum from Mie scattering theory using the online MatScat package. Excellent quantitative agreement between the low-angle scatter data and the values predicted from Mie theory were found. The results illustrate the scattering spectrum reported across the very low-angle range (from zero to ~$\theta_b$).

The measured data can be compared with theoretical models of scattering to determine the size and distribution of particles having a known refractive index.

Although various embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

What is claimed:

1. An optical vortex coronagraph scatterometer comprising:
    a light source of wavelength λ;
    a detector;
    a scattering cell in optical communication with the light source;
    a circular aperture having a radius R at a distance d from the scattering cell in optical communication with the light source;
    a pivot point between the circular aperture and the scattering cell allowing relative movement of the light source and the scattering cell with respect to the circular aperture;
    an optical vortex element;
    a first lens comprising a focal length $f_1$ disposed between the circular aperture and the optical vortex element at a distance of $f_1$ from the circular aperture and a distance of $f_1$ from the optical vortex element; and
    a second lens comprising a focal length $f_2$ disposed between the optical vortex element and the detector at a distance of $f_2$ from the detector and a distance of $f_2$ from the optical vortex element, wherein the optical vortex element is disposed between the circular aperture and the detector.

2. The scatterometer of claim 1, wherein the optical vortex element comprises a holographic element, spiral phase plate, polarization diffraction grating, or a subwavelength diffraction grating.

3. The scatterometer of claim 1, wherein the light source is a laser.

4. The scatterometer of claim 1, wherein the detector is a photodiode, CCD or CMOS sensor array.

5. The scatterometer of claim 1, further comprising a first goniometer arm having the light source and scattering cell mounted thereon.

6. The scatterometer of claim 1, further comprising a second goniometer arm having the pivot point, aperture, first lens, second lens, vortex element, and detector mounted thereon.

7. The scatterometer of claim 1, wherein the optical vortex element is capable of changing the phase of light from the light source.

8. A method for measuring the angular spectrum of scattered light, comprising:
    providing an optical vortex coronagraph scatterometer comprising:
    a light source;
    a detector;
    a scattering cell in optical communication with the light source;
    a circular aperture having a radius R at a distance d from the scattering cell in optical communication with the light source;

a pivot point between the circular aperture and the scattering cell allowing relative movement of the light source and the scattering cell with respect to the circular aperture;

an optical vortex element;

a first lens comprising a focal length f1 disposed between the circular aperture and the optical vortex element at a distance of $f_1$ from the circular aperture and a distance of $f_1$ from the optical vortex element;

a second lens comprising a focal length $f_2$ disposed between the optical vortex element and the detector at a distance of $f_2$ from the detector and a distance of $f_2$ from the optical vortex element, wherein the optical vortex element is disposed between the circular aperture and the detector;

transmitting light from the light source through the scattering cell at a first angle of the pivot point; transmitting light from the light source through the scattering cell at a second angle of the pivot point; and measuring the low-angle scattered light from the scattering cell at a plurality of angles comprising the first and second angles.

\* \* \* \* \*